United States Patent [19]

Ascher et al.

[11] Patent Number: 5,401,841
[45] Date of Patent: Mar. 28, 1995

[54] PROCESS FOR THE PRODUCTION OF CEPHALOSPORINES

[75] Inventors: Gerd Ascher, Kundl; Johannes Ludescher, Breitenbach; Hubert Sturm, Innsbruck, all of Austria

[73] Assignee: Sandoz Ltd., Basle, Switzerland

[21] Appl. No.: 69,239

[22] Filed: May 28, 1993

Related U.S. Application Data

[63] Continuation of Ser. No. 848,457, Mar. 9, 1992, abandoned.

[30] Foreign Application Priority Data

Mar. 8, 1991 [AT] Austria .................................. A504/91
May 17, 1991 [AT] Austria .................................. A101/91

[51] Int. Cl.$^6$ ............................................ C07D 501/04
[52] U.S. Cl. .................................... 540/215; 540/222; 540/226
[58] Field of Search ................ 540/228, 222, 221, 215

[56] References Cited

U.S. PATENT DOCUMENTS 4,110,534  8/1978  Clark et al. ............................ 544/16
4,703,118  10/1987 Lord et al. ............................. 540/224
4,705,851  11/1987 Takaga et al. ......................... 540/215

OTHER PUBLICATIONS

Derwent No. 50795(s) Jul. 29, 1971 (abstracting Patent No. DT-2103014).

*Primary Examiner*—Nicholas Rizzo
*Attorney, Agent, or Firm*—Robert S. Honor; Melvyn M. Kassenoff; Thomas O. McGovern

[57] ABSTRACT

The invention relates to a new, economical and simple process for the production of 3-vinylcephalosporin compounds of formula

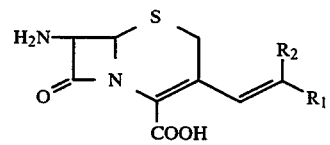

wherein $R_1$ and $R_2$ may be the same or different and denote hydrogen or an organic radical.

11 Claims, No Drawings

PROCESS FOR THE PRODUCTION OF CEPHALOSPORINES

This is a continuation of application Ser. No. 07/848,457, filed Mar. 9, 1992, now abandoned.

New process for the production of cephalosporine and novel intermediates in this process The invention relates to a new economical and simple process, via new intermediate compounds, for the production of 3-vinylcephalosporin compounds of formula I

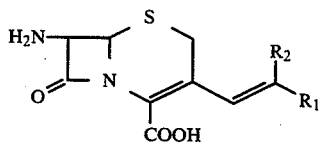

wherein $R_1$ and $R_2$ may be the same or different and denote hydrogen or an organic radical.

Compounds of formula I are useful starting products for the production of valuable 3-substituted vinyl cephalosporines.

In substituents $R_1$ and $R_2$, the organic radical may signify for example an optionally branched alkyl group or alkenyl group, a totally or partially saturated cycloalkyl radical, an optionally substituted aryl radical, aralkyl radical or a heterocycle. The radicals may be additionally substituted in any position, for example by halogen, an alkoxy or aryloxy group, a nitrogen or sulphur substituent, or a functional group such as a carbalkoxy or carboxamido group. $R_1$ and $R_2$ may also be part of an optionally substituted ring system.

In a preferred embodiment of the invention one of $R_1$ and $R_2$ is hydrogen and the other of $R_1$ and $R_2$ is i) hydrogen, lower alkyl, lower alkenyl, or lower alkinyl;

ii) lower cycloalkyl, lower cycloalkyl lower alkyl, aryl, (aryl)-lower alkyl, a heterocyclic group or a heterocyclyl-(lower)-alkyl, the ring of which may be optionally substituted by one or more (e.g. up to 3) lower alkoxy, lower alkylthio, halogen, lower alkyl, nitro, hydroxy, acyloxy, carboxy, carbalkoxy, lower alkylcarbonyl, lower alkylsulfonyl, lower alkoxysulfonyl, amino-(lower)-alkyl amino or acylamido groups, iii) a group of formula —$CH_2Z$, wherein Z has the following meanings:

a) hydroxy, lower alkoxy, formyloxy, acetyloxy, lower alkylsulfonyloxy, halogen, N-mono(-lower)alkylcarbamoyloxy, N,N-di(lower)alkylcarbamoyloxy, b) a heterocyclic group, c) a group of formula —$S(O)_mR_9$ wherein $R_9$ is an aliphatic, araliphatic, alicyclic, aromatic or heterocyclic group, and m is 0, 1 or 2;

d) an acyclic or cyclic ammonium group.

Suitable heterocyclic groups include single or fused heterocyclic rings having 4 to 7, preferably 5- or 6-atoms in each ring, there being up to four hetero atoms in each ring selected from oxygen, nitrogen and sulphur in each ring, which heterocyclic ring may carry 1 to 3 optional substituents selected from $(C_{1-4})$alkyl, $(C_{1-4})$alkoxy, halogen, trihalo-$(C_{1-4})$alkyl, hydroxy, oxo, mercapto, amino, carboxyl, carbamoyl, di-$(C_{1-4})$alkylamino, carboxymethyl, carbamoylmethyl, sulfomethyl and methoxycarbonylamino.

Examples of heterocycle include unsubstituted and substituted imidazolyl, diazolyl, triazolyl, tetrazolyl, thiazolyl, thiadiazolyl, thiatriazolyl, oxazolyl, oxadiazolyl, benzimidazolyl, benzoxazolyl, benzothiazolyl, triazolylpyridyl, purinyl, pyridyl, pyrimidinyl, pyridazinyl, pyrazolyl and triazinyl.

Suitable heterocycles include unsubstituted and substituted 5-hydroxy-4-pyridon-2-yl, 1,2,3-triazolyl; 1,2,4-triazolyl; tetrazolyl; oxazolyl; thiazolyl; 1,3,4-oxadiazolyl; 1,3,4-thiadiazolyl or 1,2,3-thiadiazolyl. Preferably the heterocycle is 1,5-dihydroxy-4-pyridon-2-yl, 5-hydroxy-1-methyl-4-pyridon-2-yl, 5-hydroxy-4-pyridon-2-yl, 1-methyl-1H-tetrazol-5-yl-2-methyl-1,3,4-thiadiazol-5-yl, 1-carboxymethyl-1H-tetrazol-5-yl, 6-hydroxy-2-methyl-5-oxo-2H-1,2,4-triazin-3-yl, 1,2,3-triazol-5-yl, 4-methyl-thiazol-5-yl.

Examples of a acyclic ammonium group include (1-carbamoyl-2-hydroxyethyl)dimethylammonium, (carbamoylmethyl)(ethyl)methylammonium or trimethyl ammonium.

Examples of cyclic ammonium are pyrrolidinium, which is N-substituted by alkyl, carbamoylalkyl, aminoalkyl or carboxyalkyl; pyridinium or cyclopentenopyridinium, which may be mono- or disubstituted by alkyl, halogen, hydroxy, carboxamido, alkoxycarbonyl, amino, monoalkylamino or dialkylamino.

Except where otherwise indicated organic radicals contain preferably up to 10 carbon atoms and lower refers to up to 4 carbon atoms.

A particular preferred group of compounds of formula I comprise those of formula Ia

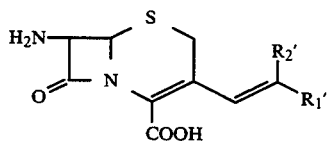

wherein one of $R_1'$ and $R_2'$ is hydrogen and the other of $R_1'$ and $R_2'$ is hydrogen, methyl, phenyl, acetoxymethyl, 4-methyl-thiazol-5-yl, N-methyl-N-ethyl-N-(carbamoylmethyl)-ammonium-methyl- or 1,5-dihydroxy-4-pyridon-2-yl.

The compounds of formula I are known and various processes for their production have been proposed.

However, according to methods known from literature, the compounds of formula I can only be produced via several intermediate steps, using extensive protecting group technology.

Thus for example, in one of such methods, 7-acylaminocephalosporanic acid which is protected by an acyl group, or a 7-benzylideneaminocephalosporanic acid which is protected by a Schiff base, is esterified with an alcohol either prior to or after the introduction of a tri-substituted phosphine or a dialkoxyphosphinyl radical in position 3. Preferably benzhydryl or p-methoxybenzyl ester are produced. These compounds are then reacted with the corresponding aldehyde, in presence of a base, to form the di-protected product. The introduction and cleavage of protecting groups in most cases requires chemical reactions using technical systems. According to another procedure, as is described for example in DE-OS 2 103 014, the methylene group in position 3 of a 7-acylamino-3-cephem-4-carboxylic acid ester is converted into an aldehyde function, and this subsequently subjected to a Wittig reaction. According to both methods, the ester group has to be chemically removed afterwards, and in a further step, depending on the choice of the acyl-protecting group, this must be chemically or enzymatically cleaved.

The functionalization of position 3 of a cephalosporin to a phosphonium salt or a dialkoxyphosphinyl derivative, which is suitable as an intermediate product for a Wittig or Horner reaction, is according to the state of the art difficult to carry out and employs several steps. For example, in DE-OS 3 307 550, the sodium salt of 7-phenylacetamido-cephalosporanic acid is saponified enzymatically to 3-hydroxymethyl-7-phenylacetamido-3-cephem-4-carboxylic acid, and subsequently reacted with diphenyldiazomethane to form 3-hydroxymethyl-7-phenylacetamido-3-cephem-4-carboxylic acid benzhydryl ester. This compound may now be converted into the corresponding phosphonium salt either directly with a reagent such as triphenylphosphonium bromide, or after exchanging the alcohol function for chlorine, with triphenylphosphine, as described in EPA 292 808. Similarly, the 3-dimethoxyphosphinyl compound may be produced via the chlorine compound, by reaction with trimethyl phosphite for example as described in Chem. Pharm. Bull. 36(7)2354 (1988).

In U.S. Pat. No. 4,705,851, 7-amino-3-hydroxymethyl-3-cephem-4-carboxylic acid, which is obtainable from 7-amino-3-acetoxymethyl-3-cephem-4-carboxylic acid by hydrolysis of the acetoxy group under conditions which may destroy the β-lactam, or by working up and splitting the corresponding cephalosporin-C analogue, is firstly reacted with salicylaldehyde to form the corresponding Schiff base, then esterified with diphenyldiazomethane and the obtained N-salicylideneamino-3-hydroxymethyl-cephem-4-carboxylic acid benzhydryl ester is converted with triphenylphosphine/iodine into the corresponding 7-salicylideneamino-3-triphenylphosphonium-methyl-cephem-4-carboxylic acid benzhydryl ester.

In a further known method a 7-acylamino-3-chloromethyl-3-cephem-4-carboxylic acid ester used as starting material for the production of a 3-vinyl-substituted cephalosporin is produced from penicillin G in a multiple step synthesis [see e.g. DE-OS 3 443 225, EPA 0 122 002 and Tetrahedron Letters 23(21)2187 (1982)]. The multiple step route in the preparation of e.g. 7-phenylacetylamino-3-chloromethyl-3-cephem-4-carboxylic acid-p-methoxybenzyl ester and the fact that the product contains only ca. 50% by weight of useable cephalosporin, make this compound an expensive intermediate product in the preparation of cephalosporins.

The above reflects the enormous difficulty in the preparation of 7-phenylacetylamino-3-chloromethyl-3-cephem-4-carboxylic acid-p-methoxybenzyl ester.

In view of the many advantages of 3-substituted vinyl cephalosporins, there was still a need for a commercially useful process starting from 7-ACA which provides intermediates from which a wide variety of 3-substituted vinyl cephalosporins can be produced. It is an object of this invention to provide an improved process for the production of compounds of formula I. It is a further object of this invention to provide certain new intermediates.

According to one aspect, the present invention provides a new process for the production of compounds of formula I as defined above, which comprises the step of i) reacting a compound of formula IV

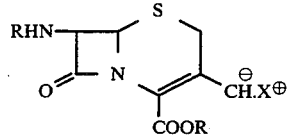

wherein R is a silyl protecting group, $X^{\oplus}$ is $-P^{\oplus}R_4)_3$ or $-P(O).(OR_4)_2.Y$, wherein $R_4$ is a lower alkyl group or an aryl group and Y is a cation of the alkali series or the protonated form of a strong organic base, with a compound of formula V

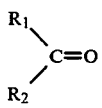

wherein $R_1$ and $R_2$ are as defined above.

Examples of silyl protecting groups include trimethylsilyl, triethylsilyl, tri-n-propylsilyl, tri-n-butylsilyl, methyldiethylsilyl, dimethylethylsilyl, phenyldimethylsilyl, tert. butyldiphenylsilyl, tert. butyldimethylsilyl and triphenylsilyl. The trimethylsilyl group is preferred.

In the definition of $R_4$ a lower alkyl group has preferably 1–4 carbon atoms. Examples of aryl include phenyl or naphthyl, optionally substituted with up to 3 groups selected from halogen, $(C_{1-4})$alkyl or $(C_{1-4})$alkoxy. Examples of a cation of the alkali series are lithium, sodium or potassium. Examples of protonated form of a strong organic base are those derived from guanidines, e.g. tetramethylguanidine, amidines, e.g. 1,8-diazabicyclo[5.4.0]undec-7-ene, 1,5-diazabicyclo[4.3.0]non-5-ene or from iminophosphoranes, e.g. 2-tert.butylimino-2-diethylamino-1,3-dimethyl-1,3,2-diazaphosphinane or tris(-dimethylamino)-(1,1,3,3-tetramethylbutyl)iminophosphorane.

The reaction can be effected in a solvent or solvent mixture which is inert under the reaction conditions, or, after adding an additional solvent, for example an inert ether such as tetrahydrofuran, diethyl ether, an ethylene glycol dialkyl ether or tert.butylmethyl ether, an inert amide such as dimethylformamide, dimethylacetamide or N-methylpyrrolidone, an urea such as tetramethylurea, 1,3-dimethyl-3,4,5,6-tetrahydro-2(1H)-pyrimidone, 1,3,2-imidazolidinone or a nitrile such as acetonitrile to produce the compound of formula IV (e.g. as described hereinafter).

The structure of the aldehyde or the ketone of formula V required to form the double bond is not critical. Representative example of $R_1$ and $R_2$ are given above. Should a substituent contain a function which is easily silylated, this should be blocked temporarily with an appropriate silylation agent prior to the reaction. E- and Z-double bond isomers may thus be produced from a aldehyde containing at least 2 carbon atoms or when using an unsymmetrical ketone. The amount of a compound of formula V may be stoichiometrical or in excess, e.g. based on the starting material of formula IV. This isomers may be separated in conventional manner, e.g. chromatography or crystallisation. This olefinization reaction may be effected within a wide temperature range. The Witrig or Horner reaction may be preferably carried out at a temperature of between −70° C. and +70° C., e.g. as described in the Examples hereinafter.

If an absolutely anhydrous system is required, a water-binding silylation agent such as N,O-bis(trimethylsilyl)acetamide, bissilylurea or mono- or bis(trimethylsilyl) trifluoroacetamide may be added to the solution of a compound of formula IV or to the aldehyde or the corresponding ketone, prior to its addition.

The compounds of formula I can be isolated in conventional manner. Any protecting groups may be removed by simple hydrolysis or alcoholysis. This may be effected e.g. either by adding the desilylation agent to the reaction mixture, or the product is extracted into a separable aqueous phase, by adding water either under alkaline or acidic conditions and precipitating by adjusting the pH value to the isoelectric point, optionally adding an organic solvent.

The compounds of formula IV are new per se and also form part of the invention.

A compound of formula IV is conveniently obtained by the step of ii) reacting a compound of formula III

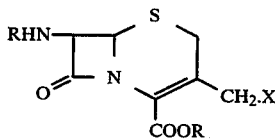   III wherein X is —P(R$_4$)$_3$I or —P(O)(OR$_4$)$_2$ and R and R$_4$ are as defined above, with a base.

Suitable bases are strong organic bases, for example guanidines e.g. tetramethylguanidine and amidines, such as DBU (1,8-diazabicyclo[5.4.0]undec-7-ene) and DBN (1,5-diazabicylo[4.3.0]non-5-ene), preferably alkali salts of nitrogen-containing compounds, such as the Li or Na salt of 1,1,1,3,3,3-hexamethyldisilazane or Li-diisopropylamide, butyllithium, hydrides of alkali metals or iminophosphoranes. The bases should be free of any moisture and should not contain any parts that can be silylated, so as to maintain the degree of disilylation of the compound. The quantity of base added corresponds approximately to the stoichiometrically calculated quantity, preferably 0.8 to 1.3 equivalents of base, based on the quantity of 7-aminocephalosporanic acid are employed. This formation of the corresponding anion may take place at low temperatures of −70° C. up to room temperature. Suitable solvents are the above-mentioned solvents or solvent mixtures, whereby the halogenated solvent is (partially) removed if necessary before adding the base.

The reaction of a compound of formula IV with a compound of formula V to the compounds of formula I is new and surprising. A silyl protecting group at an amino function greatly increases its reactivity. According to many known processes, acylation of a 6-aminopenicillanic acid or 7-aminocephalosporanic acid in the preferred form is carried out on the N,O-disilylated derivative, for example as described in U.S. Pat. No. 4,504,657. The compound of formula IV could in fact react with a compound of formula V forming a Schiff base, the resultant trimethylsilanol as a desilylation agent could protonate the existing compounds of formula IV to the starting compounds of formula III and/or simultaneously effect desilylation. As a result of the protonation and/or precipitation of the desilylated compounds due to their poor solubility, the reaction sequence III→IV→I would collapse. Thus if for example N,O-disilylated 7-aminocephalosporanic acid is allowed to stand with an excess of benzaldehyde, after some time free 7-ACA precipitates as a result of a desilylation process. Surprisingly, this reaction sequence does not occur, or only to minimal extent.

The compounds of formula III are new per se and also form part of the invention.

A compound of formula III is conveniently obtained by the step of iii) reacting a compound of formula II

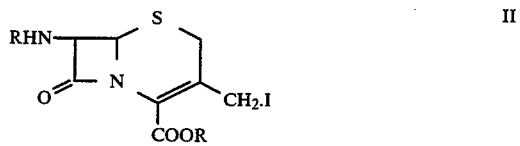

wherein R is as defined above, with a compound of formula VII or VIII

   VII

   VIII wherein R$_4$ is as defined above.

The compounds of formula II are known and may be produced by the process disclosed in AT-Patent 382 875. For example, aminocephalosporanic acid is suspended in an inert solvent and heated at reflux with an excess of silylation agent. Suitable solvents for silylation are in particular halogenated hydrocarbons. With high-boiling solvents, disilylation is effected by excessive heating in the solvent, and with low-boiling solvents silylation may be accelerated by adding organic acids, such as trifluoroacetic acid or trichloroacetic acid. Silylation can also be effected by using the nitrogen-containing silylation catalysts described in EPA 043 630. The silylation agents that may be used are preferably 1,1,1,3,3,3-hexamethyldisilazane alone or 1,1,1,3,3,3-hexamethyldisilazane in admixture with other silylation agents, such as trimethylchlorosilane, N,O-bis-(trimethylsilyl)acetamide, N-(trimethylsilyl)acetamide or the trifluoro analogues thereof or also bistrimethylsilyl urea. The disilylated compounds thus obtained are subsequently reacted with a trialkylsilyl iodide, preferably trimethyliodosilane, to form compounds of formula II as described in AT-Patent 382 875.

The compounds of formula II may then be reacted in situ with a compound of formula VII or VIII. The reaction may take place in a solvent or solvent mixture which is inert under the reaction conditions, for example in the same solvent that has been used in the previous steps. The temperature is not critical. The reaction occurs at low temperature, at room temperature or at an elevated temperature.

It will be appreciated that some of the compounds described herein e.g. those of formula IV may exist in the form of mesomers (resonance stabilized isomers) and these also fall under the definition of the formula e.g. formula IV.

The process according to the invention has great advantages compared with known processes:
1) The reaction steps i), ii) and iii) are preferably carried out in a one-pot process without isolation of the intermediates.

2) The process uses silyl groups as protecting groups, which may be introduced in a single step and also may be cleaved in one single step, thus reducing the number of steps.
3) Silyl protecting groups may be removed by simple hydrolysis or alcoholysis at the end of the reaction.
4) When the reaction is completed the object compound of formula I can be easily separated from the reaction solution.

Also the process of the present invention is characterized by low labour and energy costs. Furthermore the process can be carried out in simple manufacturing facilities and has no complicated procedures compared with known methods.

As mentioned the compounds of formula I are important starting materials for the production of valuable cephalosporin antibiotics e.g. by acylating e.g. with an appropriate acylating agent. Cephalosporins which are vinyl-substituted in 3-position are either resorbed orally, or when administered parenterally, they are characterized for their very broad, efficient spectrum of activity. The following compounds may be produced for example:

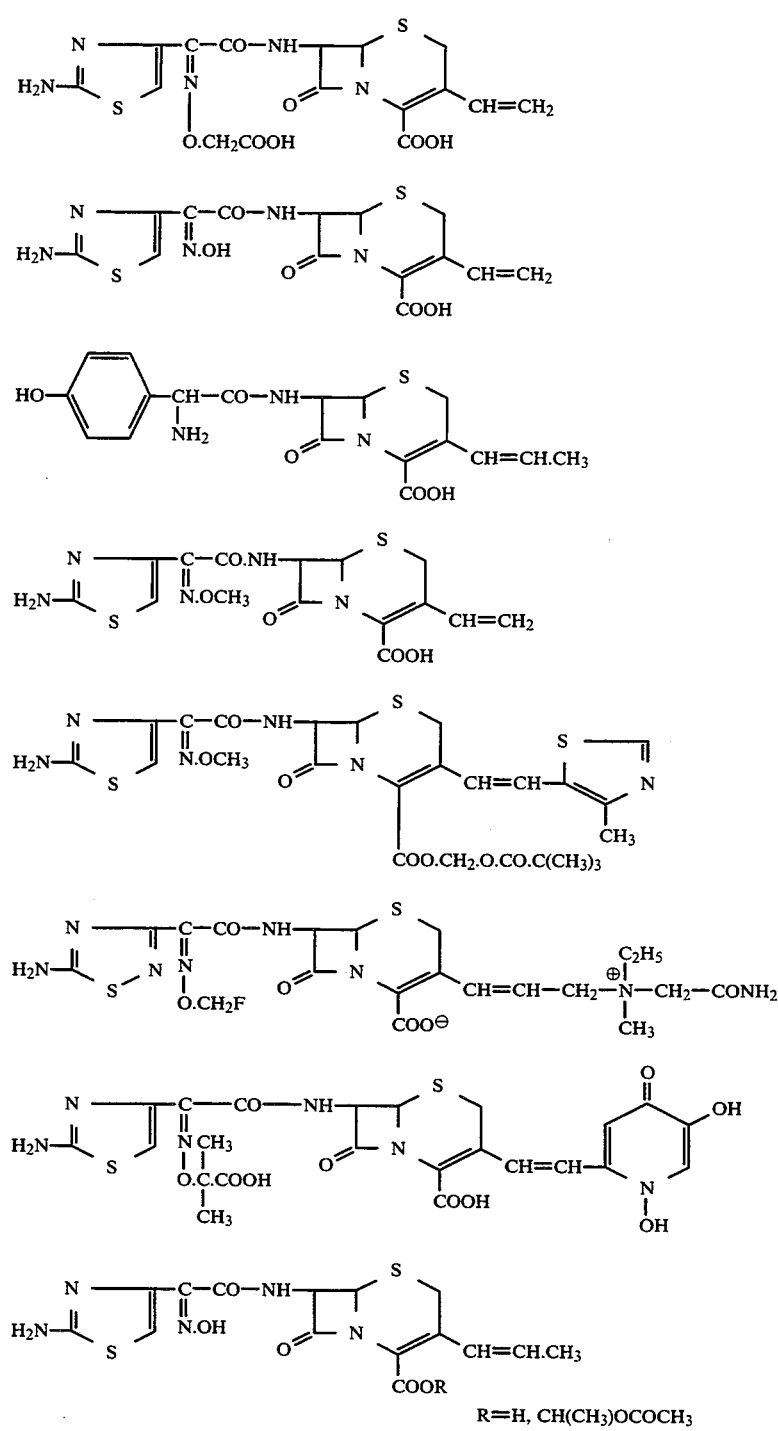

In the following examples, which illustrate the invention more fully, but in no way limit its scope, all temperatures are given in degrees celsius.

EXAMPLE 1

7-Amino-3-styryl-3-cephem-4-carboxylic acid a) 7-Trimethylsilylamino-3-triphenylphosphoniummethyl-3-cephem-4-carboxylic acid trimethylsilylester-iodide (compound of formula III)

0.8 g of dried triphenylphosphine are added at 10° to 1.53 g of 7-trimethylsilylamino-3-iodomethyl-3-cephem-4-carboxylic acid trimethylsilylester in 10 ml of hexamethyldisilazane-containing dichloromethane. The solution is subsequently stirred for one hour at this temperature. For $^1$H-NMR characterization purposes, part of the reaction solution is freed from most of the dichloromethane under vacuum, the residue is taken up in a mixture of tetrahydrofuran-$d_8$ and dichloromethane-$d_2$ and analysed.

$^1$H-NMR (THF-$d_8$/CD$_2$Cl$_2$, CH$_2$Cl$_2$ as an internal standard in ppm): 0.0068 (s, N-trimethylsilyl); 0.155 (s, COO-trimethylsilyl); 1.485 (d, J=13.4 Hz, N—H); 3.261 (AB, J=19.1 Hz, $J_{H\text{-}P}$=2.4 Hz, $J_{H\text{-}P}$=18.9 Hz, CH$_2$—S); 4.701 (dd, J=13.4 Hz, J=4.8 Hz, H$_7$); 4.923 (d, J=4.8 Hz, H$_6$); 5.247 (AB, J=14.5 Hz, $J_{H\text{-}P}$=4.5 Hz, $J_{H\text{-}P}$=16.4 Hz, CH$_2$—P); 7.574–7.858 (m, P-phenyl).

b) 7-Trimethylsilylamino-3-triphenylphosphoranylidenemethyl-3-cephem-4-carboxylic acid trimethylsilylester (compound of formula IV)

A solution of 7-trimethylsilylamino-3-triphenylphosphoniummethyl-3-cephem-4-carboxylic acid trimethylsilylester-iodide is concentrated by evaporation under vacuum, whilst excluding air and moisture. The residue is dissolved in 10 ml of dry tetrahydrofuran. A solution of 0.68 g of 1,1,1,3,3,3-hexamethyldisilazane lithium salt in 2 ml of tetrahydrofuran is added whilst cooling with ice. The colour of the solution suddenly changes to deep red. For the purpose of characterization, a small amount of the ylides is concentrated by evaporation and identified by $^1$H-NMR spectroscopy as follows in a mixture of tetrahydrofuran-$d_8$ and CD$_2$Cl$_2$:

$^1$H-NMR (THF-$d_8$/CD$_2$Cl$_2$, CH$_2$Cl$_2$ as an internal standard in ppm): 0.177 (s, COO-trimethylsilyl); 1.610 (d, J=13.5 Hz, N—H); 2.770 (AB, J=14 Hz, CH$_2$—S); 4.190 (dd, J=13.5 Hz, J=3.8 Hz, H$_7$); 4.910 (d, J=3.8 Hz, H$_6$); 7.480–7.723 (m, P-phenyl).

Isolation of this intermediate product is not necessary in order to carry out the process; the aldehyde or the ketone can be added directly.

c) 7-Amino-3-styryl-3-cephem-4-carboxylic acid (compound of formula I)

A solution of 2.4 g of trimethylsilylamino-3-triphenylphosphoniummethyl-3-cephem-4-carboxylic acid trimethylsilylesteriodide in 10 ml of absolute tetrahydrofuran is mixed at 0° with a solution of 0.70 g of 1,1,1,3,3,3-hexamethyldisilazane lithium salt in 2 ml of absolute tetrahydrofuran. 1.3 g of bistrimethylsilylacetamide and 0.68 g of benzaldehyde are added to the dark red solution. The reaction mixture is subsequently stirred over night at room temperature. The solution overlying the solid is decanted off and poured onto a mixture of ethyl acetate and diluted hydrochloric acid, whereby the product precipitates as a solid. The product is filtered off, washed with acetic ester and ether and dried.

$^1$H-NMR (CF$_3$COOD): 2.93 (AB, J=15.6 Hz, S—CH$_2$ for Z-isomer); 3.43 (AB, J=15.6 Hz, S—CH$_2$ for E-isomer); 4.89 (d, J=4.5 Hz, β-lactam-H); 5.05 (d, J=4.5 Hz, β-lactam-H); 6.41–7.29 (m, Ar—H, H—C=C—H for β-styryl-H and α-styryl-H, Z-isomer); 7.80 (d, J=17.5 Hz, α-styryl-H for E-isomer). Proportion of isomers E/Z=72/28.

EXAMPLE 2

7-Amino-3-vinyl-3-cephem-4-carboxylic acid

A solution of 2.35 g of 7-trimethylsilylamino-3-triphenylphosphoniummethyl-3-cephem-4-carboxylic acid trimethylsilylesteriodide in 10 ml of absolute tetrahydrofuran is mixed at 0° with a solution of 0.68 g of 1,1,1,3,3,3-hexamethyldisilazane lithium salt in 2 ml of absolute tetrahydrofuran. A slight excess of gaseous formaldehyde is passed into the deep red solution at 0°. The reaction mixture is subsequently diluted with ethanol and filtered. The filtrate is adjusted to pH 5.4 with acetic acid, whereby the product precipitates. The suspension is allowed to stand in a refrigerator over-night, and the product is subsequently isolated by filtration.

$^1$H-NMR (D$_2$O, DCl, TSP): 3.84 (AB, J=17.7 Hz, S—CH$_2$); 5.18 (d, J=4.5 Hz, β-lactam-H); 5.34 (d, J=4.5 Hz, β-lactam-H); 5.55 (d, J=11.4 Hz, —C=CH$_2$ cis); 5.78 (d, J=18 Hz, —C=CH$_2$ trans); 7.18 (dd, CH=C, J=11.4 Hz, J=18 Hz).

EXAMPLE 3

7-Amino-3-(prop-1-enyl)-3-cephem-4-carboxylic acid

A solution of 2.16 g of 7-trimethylsilylamino-3-triphenylphosphoniummethyl-3-cephem-4-carboxylic acid trimethylsilylesteriodide in dichloromethane is evaporated. The residue is dissolved in 8 ml of absolute tetrahydrofuran and mixed at 0° with a solution of 0.64 g of 1,1,1,3,3,3-hexamethyldisilazane lithium salt in 2 ml of absolute tetrahydrofuran. To the dark red solution is added 1.4 ml of bistrimethylsilyl acetamide, followed by 0.33 ml of anhydrous acetaldehyde. The reaction mixture is stirred over night at room temperature and subsequently mixed with the same volume of methanol. The solution is adjusted to pH 5.4 with acetic acid, whereby the product precipitates. The suspension is stirred for a further 30 minutes whilst cooling with ice, and the product is then isolated through a suction filter and dried.

$^1$H-NMR (CF$_3$COOD, TMS): 1.83 (dd, J=0.9 Hz, J=6.6 Hz, CH$_3$, Z-isomer); 2.0 (d, broad, J=6.6 Hz, CH$_3$, E-isomer); 3.65 (m, 2 AB-systems for S—CH$_2$); 5.23–5.47 (m, 4d for β-lactam-H); 6.08 (dq, J=6.6 Hz, J=12 Hz, C=CH—CH$_3$, Z-isomer); 6.40–6.79 (m, 3—CH=, Z-isomer and C=CH—CH3, E-isomer); 7.44 (dd, J=16.5 Hz, J=1.5 Hz, 3—CH=, E-isomer).

EXAMPLE 4

7-Amino-3-(prop-1-enyl)-3-cephem-4-carboxylic acid

A solution of 35 g of 7-trimethylsilylamino-3-triphenylphosphoniummethyl-3-cephem-4-carboxylic acid trimethylsilylesteriodide in dichloromethane is evaporated under vacuum to dryness. The foam resin obtained is dissolved in a mixture of 127 ml of tetrahydrofuran and 22.9 ml of N,O-bistrimethylsilyl acetamide. The solution is cooled to −20° and mixed with a solution of 7.04 g of 1,1,1,3,3,3-hexamethyldisilazane lithium salt in 35 ml of tetrahydrofuran. After 10 minutes, 21.1 ml of acetaldehyde is added and the reaction mixture is stirred for 3½ hours at 2°. The reaction mixture is subsequently evaporated on a rotary evaporator under vacuum. The residue is then taken up in 250 ml of ethyl acetate and mixed with 125 ml of water. The pH value is adjusted to 8.4 with 2N NaOH whilst cooling with ice, and the phases are separated. The ethyl acetate phase is subsequently extracted with 25 ml of water. The combined aqueous phases are extracted with 50 ml of ethyl acetate. The aqueous phase is subsequently diluted with half the volume of acetone and the pH is slowly adjusted to 3.5 with 1:1 diluted concentrated hydrochloric acid. The crystalline suspension is held in the ice bath for 3 hours whilst stirring occasionally, and the product is then filtered off. It is washed twice, each time with 25 ml of water/acetone (1/1) and 50 ml of acetone and then dried in a vacuum drying chamber.

EXAMPLE 5

7-Amino-3-(3-acetoxy-1-propen-1-yl)-3-cephem-4-carboxylic acid

A solution of 941 g of 7-trimethylsilylamino-3-triphenylphosphoniummethyl-3-cephem-4-carboxylic acid trimethylsilylesteriodide in dichloromethane is evaporated under vacuum. The foam resin obtained is dissolved in a mixture of 3900 ml of tetrahydrofuran and 617 ml of N,O-bistrimethylsilyl acetamide. The solution is cooled to $-25°$ and mixed with a solution of 178 g of 1,1,1,3,3,3-hexamethyldisilazane lithium salt in 325 ml of absolute tetrahydrofuran. It is subsequently cooled to $-30°$ and then 388 g of acetoxy-acetaldehyde are added. After stirring for 17 hours at $0°$, the reaction mixture is concentrated under vacuum. The residue is stirred into a mixture of 3500 ml of water and 3500 ml of acetic ester under pH control, whereby the pH value is held at 6.5 with diluted ammonia. After phase separation, the acetic ester phase is extracted with 1800 ml of water. The combined aqueous phases are extracted with 1800 ml of acetic ester. The aqueous phase is diluted with 3500 ml of acetone and subsequently stirred into 250 ml of water, whereby the pH value is held constant at 3.5 by adding diluted hydrochloric acid in drops. The crystalline suspension obtained is stirred for 3 hours on an ice bath. The product is then filtered off, washed with acetone and ether and dried in a vacuum drying chamber.

We claim:

1. In a process for the production of a 3-vinyl-cephalosporin derivative of formula I

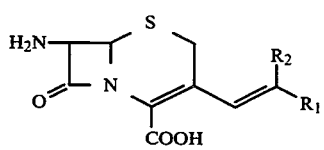

wherein $R_1$ and $R_2$ are the same or different and denote hydrogen, or a 3-vinyl-cephalosporin substituent selected from an alkyl group, alkenyl group, lower alkynyl group, lower cycloalkyl radical, (lower cycloalkyl)-lower alkyl radical, aryl radical, aralkyl radical, heterocycle radical, and heterocyclic alkyl radical or $R_1$ and $R_2$ form part of a 3-vinyl-cephalosporin ring system, by means of a Wittig reaction comprising the steps of i) reacting a compound of formula II

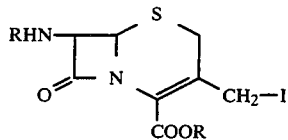

wherein R is a protecting group, with a compound of formula VII of VIII

P(R$_4$)$_3$      VII

P(OR$_4$)$_3$      VIII where $R_4$ is a lower alkyl or an aryl group, to produce a compound of formula III

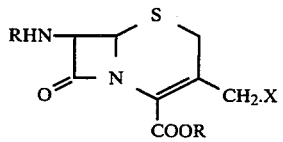

where X is $-P(R_4)_3I$ or $-P(O)(OR_4)_2$ and R and $R_4$ are as defined above;

ii) reacting the compound of formula III with a base to produce a compound of formula IV

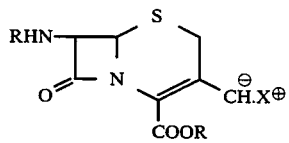

where R is as defined above and is X$^+$ $-P(R_4)_3$ or $-P(O)(OR_4)_2Y^+$, where $R_4$ is as defined above and Y is an alkali metal cation or the protonated form of a strong organic base; and iii) reacting the compound of formula IV with a compound of formula V

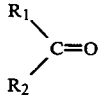

where $R_1$ and $R_2$ are as defined above, the improvement which comprises reacting a silyl protected compound of formula II'

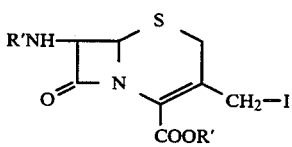

where R' is a silyl protecting group, with the compound of formula VII or VIII in step i) and following step iii) removing the protecting groups by hydrolysis or alcoholysis to produce the compound of formula I.

2. In a process for the production of a 3-vinyl- cephalosporin derivative of formula I

13

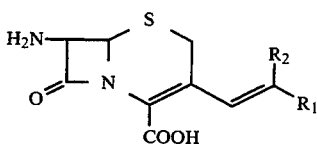

wherein one of $R_1$ and $R_2$ is hydrogen and the other is
  i) lower alkyl, lower alkenyl, or lower alkynyl;
  ii) lower cycloalkyl, (lower cycloalkyl)-lower alkyl, aryl, (aryl)-lower alkyl, a heterocyclic group or (heterocyclyl)-lower alkyl, the ring of each of which is optionally substituted by 1 to 3 substituents selected from lower alkoxy, lower alkylthio, halogen, lower alkyl, nitro, hydroxy, acyloxy, carboxy, carbalkoxy, lower alkylcarbonyl, lower alkylsulfonyl, lower alkoxysulfonyl, amino-(lower)-alkyl amino, and acylamido; or
  iii) a group of formula —$CH_2Z$, wherein Z is:
    a) hydroxy, lower alkoxy, formyloxy, acetyloxy, lower alkylsulfonyloxy, halogen, N-mono(-lower)alkylcarbamoyloxy, or N,N-di(lower)alkylcarbamoyloxy,
    b) group of formula —$S(O)_mR_9$ wherein $R_9$ is an aliphatic, araliphatic, alicyclic, aromatic or heterocyclic group, and m is 0, 1 or 2, or
    c) an acyclic or cyclic ammonium group, by means of a Wittig reaction comprising the steps of
  i) reacting a compound of formula II

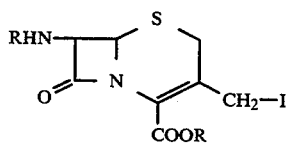

wherein R is a protecting group for a Wittig reaction, with a compound of formula VII of VIII

P($R_4$)$_3$                VII

P(O$R_4$)$_3$               VIII where $R_4$ is a lower alkyl or an aryl group, to produce a compound of formula III

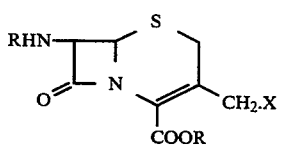

where X is —P($R_4$)$_3$I or —P(O) (O$R_4$)$_2$ and R and $R_4$ are as defined above;
  ii) reacting the compound of formula III with a base to produce a compound of formula IV

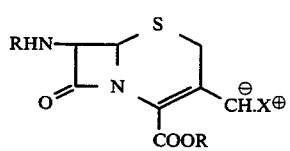

where R is as defined above and X+ is —P+($R_4$)$_3$ or —P(O) (O$R_4$)$_2$Y+, where $R_4$ is as defined above and Y is an alkali metal cation or the protonated form of a strong organic base; and
  iii) reacting the compound of formula IV with a compound of formula V

where $R_1$ and $R_2$ are as defined above, the improvement which comprises reacting a silyl protected compound of formula II'

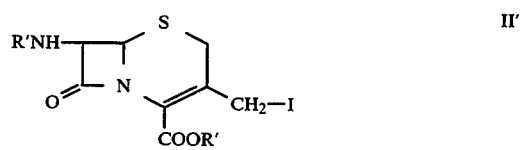

where R' is a silyl protecting group,
  with the compound of formula VII or VIII in step i) and following step iii) removing the protecting groups by hydrolysis or alcoholysis to produce the compound of formula I.

3. A process according to claim 1 in which steps i), ii) and iii) are effected in the same reaction vessel.

4. A process according to claim 1 wherein one of $R_1$ and $R_2$ is hydrogen and the other of $R_1$ and $R_2$ is hydrogen, methyl, phenyl, 3-acetoxymethyl, 4-methyl-1,3-thiazol-5-yl, N-methyl-N-ethyl-N-(carbamoylmethyl)-ammonium-methyl- or 1,5-dihydroxy-4-pyridon-2-yl.

5. A process according to claim 1 wherein the silyl protecting groups are selected from trimethylsilyl, triethylsilyl, tri-n-propylsilyl, tri-n-butylsilyl, methyldiethylsilyl, dimethylethylsilyl, phenyldimethylsilyl, tert-butyldiphenylsilyl, tert-butyldimethylsilyl and triphenylsilyl.

6. A process according to claim 1 in which, in step ii) and iii), the protonated form of the strong organic base is derived from tetramethylguanidine, 1,8-diazabicyclo-[5.4.0]undec-7-ene, 1,5-diazabicyclo[4.3.0]non-5-ene, 2-tert-butylimino-2-diethylamino-1,3-dimethyl-1,3,2-diazaphosphinane or tris(dimethylamino)-(1,1,3,3-tetramethylbutyl)iminophosphorane.

7. A process according to claim 1 in which, in step ii), the base is selected from tetramethylguanidine, 1,8-diazabicyclo[5.4.0]undec-7-ene, 1,5-diazabicylo-[4.3.0]non-5-ene, Li and Na salts of 1,1,1,3,3,3-hexamethyldisilazane, or Li-diisopropylamide, butyllithium, hydrides of alkali metals and iminophosphoranes.

8. A process according to claim 1 in which $R_4$ is ($C_{1-4}$)alkyl, phenyl, or naphthyl, or phenyl or naphthyl mono-, di-, or tri-substituted by substituents to selected from halogen, ($C_{1-4}$)alkyl, and ($C_{1-4}$)alkoxy.

9. A process according to claim 1 in which step iii) is carried out under anhydrous conditions.

10. A process according to claim 9 in which step iii) is carried out in the presence of a water-binding silylation agent.

11. A process according to claim 10 in which the water-binding silylation agent is N,O-bis(trimethylsilyl) acetamide, bissilylurea or mono or bis (trimethylsilyl) trifluoroacetamide.

* * * * *